United States Patent
Hoppe et al.

(10) Patent No.: US 6,503,523 B2
(45) Date of Patent: Jan. 7, 2003

(54) SKIN CARE AGENTS CONTAINING COMBINATIONS OF ACTIVE AGENTS CONSISTING OF VITAMIN A DERIVATIVES AND UBI- OR PLASTOQUINONES

(75) Inventors: Udo Hoppe, Heidmühlen (DE); Volker Schreiner, Hamburg (DE); Franz Stäb, Echem (DE)

(73) Assignee: GS Development A.B., Malmo (SE)

( * ) Notice: Subject to any disclaimer, the term of this patent is extended or adjusted under 35 U.S.C. 154(b) by 0 days.

(21) Appl. No.: 10/132,214

(22) Filed: Apr. 26, 2002

(65) Prior Publication Data

US 2002/0182199 A1 Dec. 5, 2002

Related U.S. Application Data

(63) Continuation of application No. 09/674,721, filed as application No. PCT/EP99/02854 on Apr. 28, 1999, now abandoned.

(30) Foreign Application Priority Data

May 7, 1998 (DE) .......................... 198 20 392

(51) Int. Cl.$^7$ ............................ A61K 7/00; A61K 31/07

(52) U.S. Cl. ........................ 424/401; 424/400; 514/725; 514/844; 514/863; 514/864

(58) Field of Search ................................ 424/400, 401; 514/725, 844, 863, 864

(56) References Cited

U.S. PATENT DOCUMENTS

| | | |
|---|---|---|
| 4,966,965 A | 10/1990 | DeLuca et al. |
| 5,362,494 A | 11/1994 | Zysman et al. |
| 5,378,461 A | 1/1995 | Neigut |
| 5,889,062 A | 3/1999 | Hoppe et al. |

FOREIGN PATENT DOCUMENTS

| | | |
|---|---|---|
| WO | WO 95 11015 | 4/1995 |
| WO | WO 95 26180 | 10/1995 |

*Primary Examiner*—Shelley A. Dodson
(74) *Attorney, Agent, or Firm*—Nixon & Vanderhye P.C.

(57) ABSTRACT

The invention relates to topical preparations containing one or more compounds chosen from group (A), which consists of vitamin A-acid or its derivatives, combined with one or more compounds chosen from group (B), which consists of ubiquinones and their derivatives and plastoquinones and their derivatives.

12 Claims, No Drawings

SKIN CARE AGENTS CONTAINING COMBINATIONS OF ACTIVE AGENTS CONSISTING OF VITAMIN A DERIVATIVES AND UBI- OR PLASTOQUINONES

This application is a continuation of application Ser. No. 09/674,721, filed Nov. 6, 2000 now abandoned, which in turn is a 371 of PCT/EP99/02854 filed Apr. 28, 1999, the entire content of which is hereby incorporated by reference in this application.

The invention relates to topical preparations with ubiquinones and/or plastoquinones.

The aging of the skin is caused by endogenous, genetically determined influences. Exogenous factors, such as UV light and noxious chemicals can have a cumulative effect and accelerate the natural aging process. Numerous degenerative processes occur which, depending on the extent of the influence factors, lead, amongst other things, to the following structural changes and damage to the dermis and epidermis (dermatoheliosis):

a) Retroplasia of the microvascular system.
b) Looseness and formation of wrinkles, partly due to the loss, and cross-linking, of collagen, and accumulation of glucose aminoglycane (basic substance).
c) Flattening of the reticular system. This is connected with a narrowing of the surface between dermis and epidermis, through which substances are exchanged for nourishment and purification of the epidermis.
d) Limited regenerative turnover in the epidermis, combined with defective formation of the horny layer (keratinization disorders) which leads to the drying-out of the skin.
e) Defective regulation of cell distribution (proliferation) and cell maturation (differentiation) in the epidermis, resulting in atypical cells and loss of polarity.
f) Local hyper-, hypo- and defective pigmentation (age spots).

In the pathogenesis of acne, which occurs especially in young people, but also in later life, both the over-production of sebaceous gland lipids by over-developed sebaceous glands (sebaceous gland hyperplasia) and keratinization disorders of the sebaceous gland outlet play an essential role. In both cases there is accumulation of sebum lipids that provide the breeding ground for acne-producing bacteria.

Pigmentation of the skin is due, for example, to melanocytes, which are found in the bottom layer of the epidermis, the basal stratum, next to the basal cells, which—depending on skin type—are present as pigment-forming cells either individually or in relatively large numbers. Melanocytes contain melanosomes as characteristic cell organelles, which produce more melanin when stimulated by UV radiation. This is transported into the cells of the horny layer (keratinocytes) and causes more or less pronounced brownish or brown skin colouring.

Melanin is formed as the final stage in an oxidation process, in which tyrosine, with the aid of the enzyme tyrosinase, is converted via 3,4-dihydroxyphenyl-2-aminopropionic acid (dopa), dopa-quinone, leucodopachrome, dopachrome, 5,6-dihydroxyindol and indole-5,6-quinone finally to melanin.

Problems with hyperpigmentation of the skin have many causes and/or are side effects of many biological processes, e.g. UV radiation (e.g. freckles, ephelides), genetic disposition, defective pigmentation of the skin and/or scarring during the healing of wounds, or skin aging (e.g. lentigines seniles).

Substances and preparations are known which counteract skin pigmentation. Those in practical use are essentially preparations based on hydroquinone, which however on the one hand only begin to show an effect after several weeks of use, whilst on the other hand their use over a very long period is not always safe for toxicological reasons. The inhibition of tyrosinase with substances such as koji acid, ascorbic acid, azelaic acid and their derivatives is also common, but has cosmetic and dermatological disadvantages.

The present invention relates in particular to products for the care and prophylaxis of skin aged by light or with a tendency towards acne, and for the treatment in particular of the types of damage listed under a)–f) caused by light aging and especially for cosmetic lightening ("skin whitening") of undesired skin pigmentation.

Products for the care, prophylaxis and treatment of light-aged skin and for the prophylactic treatment of acne are known. They contain, for example, vitamin A acid. Their effect on the structural damage of light-aging and/or reduction of the risk of acne is however largely limited. In addition the use of products containing vitamin A acid often causes strong erythematous skin irritations. Vitamin A acid in particular can therefore only be used in low concentrations.

Cosmetic preparations containing coenzyme Q-10 are also known from DE-A-33 09 850. This preparation is suitable for the treatment of skin diseases, the prophylaxis of dystrophic and dysmetabolic skin conditions and for application in the case of chemical and physical respiration damage or delayed respiration associated with age and wear and tear.

The published Japanese patent application 58,180,410 describes the suitability of coenzyme Q-10 for cosmetics. It is believed to activate the skin cell metabolism and suppress oxidation. Coenzyme Q-10 has proved to perform an important function in the prevention of skin damage by UV radiation and the prevention of skin aging. In 20–40 year olds, skin roughness is improved adding moisture to the skin.

From WO95/26180, topical preparations are known, which contain retinols, retinals, beta-carotene and ubiquinones or plastoquinones.

The aim of the present invention was therefore to find ways of avoiding the disadvantages of the state of the art. In particular the prophylactic effect on acne and the restructuring effect in the case of light-aging should be permanent, disadvantageous [sic] and without the risk of side effects.

According to the invention these aims are achieved by skin preparations containing vitamin A acid or its derivatives combined with ubiquinones and/or plastoquinones.

The object of the invention is topical preparations containing one or more compounds chosen from group (A), which consists of vitamin A acid or its derivatives, combined with one or more compounds chosen from group (B), which consists of ubiquinones and their derivatives and plastoquinones and their derivatives.

Preferred preparations are those containing one, two or three compounds chosen from group (A), combined with one, two or three compounds from group (B).

The inventive topical preparations can be cosmetic or dermatological preparations, and they are also described here as skin care products or dermatological products. They and their active agents are used for prophylaxis in the case of acne and for care and prophylaxis in the case of light-aging and for the treatment of light-aged skin and to lighten undesired skin pigmentation.

The object of the invention is also the use of topical preparations containing one or more compounds chosen from group (A), which consists of of vitamin A acid or its derivatives, combined with one or more compounds chosen from group (B), which consists of ubiquinones and their derivatives and plastoquinones and their derivatives, for the care and prophylactic treatment of acne and for the care and prophylaxis of light-aging and for the treatment of light-aged skin and for the lightening of undesired skin pigmentation.

The object of the invention is therefore also the use of the aforementioned preparations and active agents for the purposes described, but preferably their use for prophylaxis and treatment of the following phenomena a)–f), especially dermatoheliosis:

a) Retroplasia of the microvascular system.

b) Looseness and formation of wrinkles, partly due to the loss, and cross-linking, of the collagen, and accumulation of glucose aminoglycane (basic substance).

c) Flattening of the reticular system. This is connected with a narrowing of the surface between dermis and epidermis, through which substances are exchanged for nourishment and purification of the epidermis.

d) Limited regenerative turnover in the epidermis, combined with defective formation of the horny layer (keratinization disorders) which leads to the drying-out of the skin.

e) Defective regulation of cell distribution (proliferation) and cell maturation (differentiation) in the epidermis, resulting in atypical cells and loss of polarity.

f) Local hyper-, hypo- and defective pigmentation (age spots).

The term "vitamin A acid and its derivatives" covers all-trans retinoic acid, also known as tretinoin, and its isomers, erg. 13-cis retinoic acid or isotretinoin and their repective derivatives. Derivatives also include, for example, compounds in which the carboxylic acid groups are esterified with alcohols. Isomers of the all-trans retinioc acid shall be understood to mean compounds in which one or more, e.g. up to three double bonds are present in cis-configuration instead of trans-configuration.

Suitable derivatives of the inventive vitamin A acids on its derivatives are in particular the salts. Esters of the carboxylic acid groups of these inventive compounds with alcohols are also preferred.

Preferred salts are water-soluble salts, e.g. sodium, potassium and ammonium salts or calcium salts.

Suitable esters are for example those formed with short-chained or medium-chained alkanols, preferably with mono-alcohols. These can be straight-chained or branched and possess e.g. 1–12, preferably 1–6 carbon atoms. Methanol, ethanol, n-propanol and iso-propanol are preferred.

Their alkyl residues can also be mono- or polyunsaturated and e.g. possess one, two or three double bonds.

Further suitable alcohols with which inventive esters are formed are retinols and alpha-tocopherols with which e.g. retinol retinoate or DL-alpha-tocopheryle-retinoate (tocoretinate) are contained.

Preferred compounds of group (B) are ubiquinones and their derivatives.

Preparations containing all-trans retinoic acid and coenzyme $Q_{10}$ are especially preferred.

Ubiquinones (also coenzyme $Q_n$) are a group of substances that have n isoprene units bounded to their quinone ring in a chain ($Q_0$–$Q_{10}$). Ubiquinones function as electron carriers during biological, mitachondral oxidation, and thus play a significant role in energy metabolism of the cells. Plastoquinones are similar plant-based compounds, which play a role in photosynthesis. In cosmetic preparations ubiquinones have long been used as antioxidants to protect substances sensitive to oxidation from oxygen-radical-induced decomposition.

The terms "ubiquinones" and "plastoquinones" are here also intended to refer to "ubiquinones and their derivatives" and "plastoquinones and their derivatives".

The ubiquinones are known from the literature (e.g. "Römpp Chemie Lexikon, Georg Thieme Verlag, Stuttgart, New York, 9th edition, p. 4784–4785 or "The Merck Index", 11th edition, Merck & Co. Inc. Rahway, N.Y., USA, Abstr. 9751 (1989)). They are also referred to as mitoquinones or coenzyme Q. The number of isoprene units in the side chain is indicated by n in the expression coenzyme $Q-_n$, in which n means an integer. Ubiquinones or coenzyme $Q-_n$ with n=0–12 are preferred, especially n=1–12, and ideally n=6–10. An object of the invention is thus also the quinone fundamental substance of the ubiquinone without isoprene substituents.

Inventive ubiquinones or their derivatives also include, e.g., alkyl ubiquinones, especially 6-alkyl-ubiquinones, with preferably $C_1$–$C_{12}$-alkyl residues. Decyl-ubiquinone is preferred, especially 6-decyl-ubiquinone or 2,3-dimethoxy-5-methyl-6-decyl-1,4-benzoquinone.

The plastoquinones are also known from the literature (e.g. "Römpp Chemie Lexikon", Georg Thieme Verlag, Stuttgart, N.Y., 9th edition, p. 3477). In structure they are closely related to the ubiquinones and also belong to the isoprenoid quinones, as they have a side chain of isoprene units on the quinone ring. Plastoquinones with 0–12 are preferred, especially 1–10, and ideally 6–10 isoprene units in the side chain. An object of the invention is therefore also the quinone parent substance of the plastoquinone without isoprene substituents.

Inventive plastoquinones or their derivatives are e.g. alkyl-plastoquinones with preferably $C_1$–$C_{12}$-alkyl residues. Decyl-plastoquinones are preferred, especially 5- or 6-decyl-plastoquinones, or 2,3-dimethyl-5-decyl-1,4-benzoquinone.

Ubiquinones function as electron carriers in biological, mitochondral oxidation, and thus play a significant role in the energy metabolism of animal cells. In cosmetic preparations ubiquinones have long been used as antioxidants to protect substances sensitive to oxidation.

Plastoquinones are similar compounds from the plant kingdom, which play a role during photosynthesis in the chloroplasts of plant cells. They differ from the ubiquinones in having three substituents on the quinone ring, with the two methoxy groups in the ubiquinones being replaced by methyl groups and a methyl group by a hydrogen atom. However the chain-form bonded isoprene units are structurally identical (cf. e.g. Pfister and Arntzen, Z. für Naturforschung, C34; 996 ff. 1979).

The following inventive active agents and combinations with these are especially preferred:

coenzyme Q-10, coenzyme Q-9, coenzyme Q-8, coenzyme Q-7, coenzyme Q-6, plastoquinones with 10 isoprene units (also called PQ-10 in accordance with the IUB abbreviation PQ for plastoquinone, in the formula PQ-n, n indicates the number of isoprene units (0–12)), PQ-9, PQ-8, PQ-7, PQ6.

Vitamin A Acid (Tretinoin)

It has surprisingly been shown that vitamin A acid or its derivatives, act synergically in combination with ubiquinones and/or plastoquinones in acne prophylaxis and/or protection from light-aging and/or the repair of structural damage of the skin caused by light, which significantly remedies the disadvantage of the state of the art. The inventive active agent combination and topical preparations are also highly suitable for lightening undesired pigmentation of the skin, also acting proplylactically.

It is especially advantageous that, in the inventive combinations the quantities of vitamin A acid normally used in topical preparations can be reduced, without any reduction in effectiveness. In addition the stability of the vitamin A acid is increased in the preparations by the constituents (B), increasing shelf life.

The term "pigmentation" (or "pigmented") shall mean any discoloration of the (or discolored) skin.

Prevention or also prophylaxis and treatment of undesired pigmentation of the skin also includes, for example, the lightening of dark skin, but also the lightening or removal of hyperpigmentations, especially local hyperpigmentations and defective pigmentations, also known, e.g. by the term "skin-whitening (effect)" and also preventive applications for these purposes.

Also included under prevention or prophylaxis and treatment of undesired pigmentation of the skin are prevention and treatment of skin-browning, especially skin-browning caused by UV radiation.

Suitable concentrations of vitamin A acids or their derivatives within the meaning of the invention in topical preparations are preferably between 0.0001 and 10 wt. %. The effective concentrations of ubiquinones and/or plastoquinones in topical preparations are preferably between 0.001 and 90 wt. %.

It is advantageous for the inventive skin care products or dermatological products to contain combinations made up as follows:

0.0001–1 wt. % vitamin A acid or its derivatives 0.001–10 wt. % ubiquinone and/or plastoquinone.

Skin care products or dermatological products preferably contain:

0.001–1 wt. % vitamin A acid or its derivatives 0.01–1 wt. % ubiquinone and/or plastoquinone, especially 0.001–1 wt. % all-trans retinoic acid 0.01–1 wt. % coenzyme $Q_{10}$.

Ideally the skin care products or dermatological products contain 0.01 wt. % all-trans retinoic acid 0.3 wt. % coenzyme $Q_{10}$.

Within the framework of the application, weight percentages relate to 100% total composition of the inventive skin care preparation or dermatological product in question.

The inventive active agent combinations or active agents can be present in the topical preparations in quantities of 0.0001–99 wt. % e.g. also in quantities of 0.001–50 wt. %, relative to the total weight of the preparations in each case.

The inventive active agent combinations or active agents can preferably be present in the topical preparations in quantities of 0.01–10 wt. %, especially in quantities of 0.1–1 wt. %, relative to the total weight of the preparations in each case.

In the combinations, the weight ratios (A):(B) of the two constituents can vary widely, e.g. in the ratio 1:100–1:1, preferably in the ratio 1:15–1:1. They can also be present e.g. in the weight ratio 1:2 to 1:1 or 1:1.

Inventive topical preparations or compositions with the inventive combinations and active agents are all common forms of application, e.g. cremes (W/O, O/W, W/O/W), gels, lotions, milks.

The inventive topical preparations can be formulated as liquid, pasty, or solid preparations, for example as aqueous or alcoholic solutions, aqueous suspensions, emulsions, ointments, cremes, oils, powders or sticks. Depending on the desired formulation, active agents can be incorporated into pharmaceutical and cosmetic bases for topical applications, which contain as further constituents, for example, oil constituents, fat and wax, emulsifiers, anionic, cationic, ampholytic, zwitterionic and/or nonionic tensides, low mono- and polyvalent alcohols, water, preservatives, buffer substances, thickening agents, perfumes, dyes and cloudifiers. The inventive substances can also be used advantageously in transdermal therapeutic systems, especially cubic systems.

It is also advantageous to add antioxidants (e.g. alpha-tocopherol, vitamin A and vitamin C, imidazols, alpha-hydroxycarboxylic acids (e.g. malic acid, glycolic acid. gluconic acid, salicylic acid and their derivatives) and/or iron chelating agents (e.g. EDTA, alpha-hydroxy fatty acids) and/or known UV light protection filters in quantities of e.g. 0.1–10 wt. %, to the preparations, to guarantee the stability of the substances sensitive to oxidation.

It is also advantageous to add especially 0.01–10 wt. % of substances/substance combinations of the aerobic cellular energy metabolism (e.g. cellular energy transfer agents such as creatine, guanine, guanosine, adenine, nicotine, nicotinamide, riboflavin), coenzymes (e.g. pantothenic acid, panthenol, liponic acid, niacin), auxiliary factors (e.g. L-carnitine, uridine), substrates, (e.g. hexoses, pentoses, fatty acids) and intermediate products of metabolism (e.g. citric acid, pyuvate) and/or glutathion to the preparations.

The inventive preparations can also advantageously contain substances that absorb the UV radiation in the UVA and/or UVB range, with the total quantity of filter substances amounting to e.g. 0.1 wt. %–30 wt. %, 0.5–10 wt. %, and especially 1.0–6.0 wt. %, relative to the total weight of the preparations, in order to produce cosmetic preparations that protect the skin from the whole range of ultra-violet radiation. They can also be used as sunscreens for the skin. In contrast to the active agents in the preparations, the UV absorbers work as antioxidants.

If the inventive emulsions contain UVB filter substances, these can be oil-soluble or water-soluble. Advantageous oil-soluble UVB filters according to the invention include e.g.:

3-benzylidene camphor derivatives, preferably 3-(4-methylbenzylidene) camphor. 3-benzylidene camphor.

Advantageous water-soluble UVB filters include e.g.:

salts of 2-phenylbenzimidazene-5-sulfonic acid and their sodium, potassium or their triethanol ammonium salt, as well as the sulfonic acid itself.

It can also be advantageous to combine inventive active agent combinations with UVA filters, which up to now have usually been contained in cosmetic preparations. These substances are preferably derivatives of dibenzoylmethane, especially 1-(4'-tert.butylphenyl)-3(4'-methoxyphenyl) propane-1,3-dione and 1-phenyl-3-(4'-isopropyl-phenyl) propane-1,3-dione. These combinations and/or preparations which contain these combinations are also an object of the invention. The quantities utilized for the UVB combination can be used.

A further object of the invention is thus the combinations of the inventive substances, especially in the topical preparations, with antioxidants, substances of aerobic cellular energy metabolism and/or UV absorbers, which can improve, for example, the stability and the effectiveness of the preparation.

In addition, protective formulation forms can be used, in which the inventive substances are enclosed (encapsulated) in, for example, liposomes, micelles, nanospheres, etc. made from, for example, hydrated amphiphiles, such as ceramides, fatty acids, sphingomyeline and phosphoglycerides, or in cyclodextranes. Further protection can be achieved by the use of protective gas (e.g. $N_2$, $CO_2$) in the formulation and the use of gas-proof forms of packaging.

Further auxiliary substances and additives may be water-binding substances, thickeners, fillers, perfume, dyes, emulsifiers, active agents such as vitamins, preservatives, water and/or salts.

During processing of the active agents and other substances sensitive to oxidation, the temperature should not exceed 40° C. Otherwise the usual rules known to the skilled person are to be complied with.

The inventive groups of compounds can thus be incorporated into all bases. However W/O and O/W and W/O/W emulsions are preferred in principle. Inventive combinations can be used especially advantageously in products such as, for example O/W cremes, W/O cremes, O/W lotions or W/O lotions.

Indications of quantities, percentage indications or parts relate, unless otherwise indicated, in particular to the total weight of the preparations or the mixture in question.

The following examples serve to describe the invention, without intending to restrict the invention to these examples. The quantity indications are parts by weight or weight percentages relative to the "100" indications.

EXAMPLE I

| Skin creme of the W/O type | |
| --- | --- |
| Vaseline DAB 9 | 13 |
| Glycerine DAB 9 | 6.3 |
| Water VES | 34.4 |
| Paraffin oil (Mineral oil 5E, Shell | 31 |
| Cetearyl alcohol/TEG-40-castor oil/sodium cetearyl sulfate (Eutanol G, Henkel KGaA) | 2.5 |

0.3 parts coenzyme $Q_{10}$ dissolved in 3 parts paraffin oil are incorporated into the warm fat phase at 75° C. The fat phase is then added to the warm water phase at 75° C., stirred and homogenized until a smooth, light yellow creme is produced. 0.03 parts all-trans retinal acid are dissolved into a further 3.47 parts paraffin oil at room temperature and stirred into the cooled creme.

Example I has the following final composition:

| | |
| --- | --- |
| Vaseline DAB 9 | 13 |
| Glycerine DAB 9 | 6.3 |
| Water VES | 34.4 |
| Paraffin oil (Mineral oil 5E, Shell) | 43.47 |
| Cetearyl alcohol/TEG-40-castor oil/sodium cetearyl sulfate (Eutanol G, Henkel KGaA) | 2.5 |
| All-trans retinoic acid | 0.03 |
| Coenxyme $Q_{10}$- | 0.3 |
| | 100 |

EXAMPLE II

| Skin creme of the W/O type | |
| --- | --- |
| PEG-1 glyceryl oleostearate + paraffin wax | 8 |
| Vaseline DAB | 2.8 |
| Paraffin wax/paraffin | 1.8 |
| Ceresin | 2.2 |
| Octyl dodecanol | 10 |
| Propylene glycol | 1 |
| Glycerine | 1 |
| Magnesium sulfate | 0.7 |
| Water VES | 59.7 |
| Total additives (perfume, preservative, stabilizer) | 0.8 |

0.2 parts coenzyme $Q_{10}$ and 0.2 parts coenzyme $Q_6$ dissolved in 6 parts paraffin oil are incorporated into the warm fat phase at 75° C. The fat phase is then added to the warm water phase at 75° C., stirred and homogenized until a smooth, light yellow creme is produced. 0.02 parts all-trans retinoic acid are dissolved into a further 5.88 parts paraffin oil at room temperature and stirred into the cooled creme.

Example II has the following final composition:

| | |
| --- | --- |
| PEG-1 glyceryl oleostearate + paraffin wax | 8 |
| Vaseline DAB | 2.8 |
| Paraffin wax/paraffin | 1.8 |
| Paraffin oil (Mineral oil 5E, Shell) | 11.88 |
| Ceresin | 2.2 |
| Octyl dodecanol | 10 |
| All-trans retinoic acid | 0.02 |
| Coenzyme $Q_6$ | 0.2 |
| Coenzyme $Q_{10}$ | 0.2 |
| Propylene glycol | 1 |
| Gycerine | 1 |
| Magnesium sulfate | 0.7 |
| Water VES | 59.4 |
| Total additives (perfume, preservative, stabilizer) | 0.8 |
| | 100 |

EXAMPLE III

| Skin creme of the O/W type | |
| --- | --- |
| Octyl dodecanol (Emulgade F, Henkel KGaA) | 9.3 |
| Cetearyl alcohol/TEG-40-castor oil/sodium cetearyl sulfate (Eutanol G, Henkel KGaA) | 3.7 |
| Water VES | 73.7 |
| Glycerine DAB 9 | 4.6 |

0.9 parts coenzyme $Q_{10}$ dissolved in 4 parts paraffin oil are incorporated into the warm fat phase at 75° C. The fat phase is then added to the warm water phase at 75° C., stirred and homogenized until a smooth, light yellow creme is produced. 0.01 parts all-trans retinioc acid are dissolved into a further 3.79 parts paraffin oil at room temperature and stirred into the cooled creme.

Example III has the following final composition:

| | |
|---|---|
| Octyl dodecanol (Emulgade F, Henkel KGaA) | 9.3 |
| Cetearyl alcohol/TEG-40-castor oil/sodium cetearyl sulfate (Eutanol G, Henkel KGaA) | 3.7 |
| Water VES | 73.7 |
| Glycerine DAB 9 | 4.6 |
| Paraffin oil (Mineral oil eE, Shell) | 7.79 |
| Coenzyme $Q_{10}$ | 0.9 |
| All-trans retinoic acid | 0.01 |
| | 100 |

EXAMPLE IV

| O/W Lotion | |
|---|---|
| Steareth-2 | 3 |
| Steareth-21 | 2 |
| Cetearyl alcohol/TEG-40-castor oil/sodium cetearyl sulfate (Eutanol G, Henkel KGaA) | 2.5 |
| Propylene glycol | 1 |
| Glycerine | 1 |
| Water VES | 74.3 |
| Total additives (perfume, preservative, stabilizer) | 0.8 |

0.1 parts coenzyme $Q_{10}$ dissolved in 5.2 parts paraffin oil are incorporated into the warm fat phase at 75° C. The fat phase is then added to the warm water phase at 75° C., stirred and homogenized until a smooth, light yellow creme is produced. 0.05 parts all-trans retinoic acid are dissolved into a further 9.85 parts paraffin oil at room temperature and stirred into the cooled lotion.

Example IV has the following final composition:

| | |
|---|---|
| Steareth-2 | 3 |
| Steareth-21 | 2 |
| Cetearyl alcohol/TEG-40-castor oil/sodium cetearyl sulfate (Eutanol G, Henkel KGaA) | 2.5 |
| Paraffin oil (Mineral oil eE, Shell) | 14.85 |
| Propylene glycol | 1 |
| Coenzyme $Q_{10}$ | 0.1 |
| All-trans retinoic acid | 0.05 |
| Glycerine | 1 |
| Water VES | 74.3 |
| Total additives (perfume, preservative, stabilizer) | 0.8 |
| | 100 |

EXAMPLE V

| O/W Lotion | |
|---|---|
| Octyl dodecanol (Emulgade F, Henkel KGaA) | 5.6 |
| Cetearyl alcohol/TEG-40-castor oil/sodium cetearyl sulfate (Eutanol G, Henkel KGaA) | 8.9 |
| Cetearyl isononanoate (Cetiol 5N, Henkel KGaA) | 7.5 |
| Water VES | 62.3 |
| Glycerine DAB 9 | 4.7 |

0.4 parts coenzyme $Q_{10}$ dissolved in 6 parts paraffin oil are incorporated into the warm fat phase at 75° C. The fat phase is then added to the warm water phase at 75° C., stirred and homogenized until a smooth, light yellow creme is produced. 0.04 parts all-trans retinoic acid are dissolved into a further 4.56 parts paraffin oil at room temperature and stirred into the cooled lotion.

Example V has the following final composition:

| | |
|---|---|
| Octyl dodecanol (Emulgade F, Henkel KGaA) | 5.6 |
| Cetearyl alcohol/TEG-40-castor oil/sodium cetearyl sulfate (Eutanol G, Henkel KGaA) | 8.9 |
| Cetearyl isononanoate (Cetiol 5N, Henkel KGaA) | 7.5 |
| Water VES | 62.3 |
| Glycerine DAB 9 | 4.7 |
| Paraffin oil (Mineral oil eE, Shell) | 10.56 |
| Coenzyme $Q_{10}$ | 0.4 |
| All-trans retinoic acid | 0.04 |
| | 100 |

EXAMPLE VI

| Skin oil | |
|---|---|
| Glyceryl tricaprylate (Miglyol 812, Dynamit Nobel) | 21 |
| Hexyllaurate (Cetiol A, Henkel KGaA) | 20 |
| Octyl stearate (Cetiol 886, Henkel KGaA) | 20 |
| Paraffin oil (Mineral oil 5E, Shell) | 36.98 |
| All-trans retinoic acid | 0.02 |
| Coenzyme $Q_6$ | |
| Coenzyme $Q_{10}$ | 0.4 |
| | 100 |

The constituents are stirred at 25° C., until a smooth, clear mixture is produced.

EXAMPLE VII

| Skin oil | |
|---|---|
| Glyceryl tricaprylate (Miglyol 812, Dynamit Nobel) | 21 |

-continued

| Skin oil | |
|---|---|
| Hexyllaurate | 20 |
| (Cetiol A, Henkel KGaA) | |
| Octyl stearate | 20 |
| (Cetiol 886, Henkel KGaA) | |
| Paraffin oil | 36.98 |
| (Mineral oil 5E, Shell) | |
| Tocoretinate | 0.02 |
| Coenzyme $Q_{10}$ | 2.0 |
| | 100 |

What is claimed is:

1. A method for treating and preventing acne, light-aging, light-aged skin, and undesired pigmentation of the skin, comprising topically applying to skin to be treated a composition containing:
one or more compounds of group (A), which consists of vitamin A acid, all-trans retinoic acid, retinoic acid, isomers of retinoic acid, in which isomers one or more double bonds are present in cis-configuration instead of trans configuration, esters of the aforementioned compounds, where carboxylic acid groups are esterified with alcohols, and salts of the aforementioned compounds,
wherein the quantity of the compound(s) of group (A) is reduced while maintaining effectivity of the method, if the compound(s) of group (A) is(are) combined with one or more compounds of group (B), which consists of ubiquinones, plastoquinones and derivatives thereof.

2. The method of claim 1, wherein the reduction of the quantity of the compound(s) of group (A) reduces the occurrence of erythematous skin irritations.

3. The method of claim 1, wherein the retinoic acid isomer is 13-cis retinoic acid.

4. The method of claim 1, wherein the compound of group (A) is all-trans retinoic acid, and wherein the compound of group (B) is coenzyme $Q_{10}$.

5. The method of claim 1, wherein the weight ratio of the compound(s) of group (A) and the compound(s) of group (B) is between 1:100 and 1:1.

6. The method of claim 1, wherein the composition contains between 0.0001 and 0.05 weight percent of the compound(s) of group (A).

7. A method for increasing the stability of a compound of group (A) comprising:
vitamin A acid, all-trans retinoic acid, retinoic acid, isomers of retinoic acid, in which isomers one or more double bonds are present in cis-configuration instead of trans configuration, esters of the aforementioned compounds, where carboxylic acid groups are esterified with alcohols, and salts of the aforementioned compounds,
in topical compositions containing one or more compounds of group (A),
by adding one or more compounds of group (B), which consists of ubiquinones, plastoquinones and derivatives thereof.

8. The method of claim 7, wherein increasing the stability of the compound(s) of group (A) increases the shelf life of the composition.

9. The method of claim 7, wherein the retinoic acid isomer is 13-cis retinoic acid.

10. The method of claim 7, wherein the compound of group (A) is all-trans retinoic acid, and wherein the compound of group (B) is coenzyme $Q_{10}$.

11. The method of claim 7, wherein the weight ratio of the compound(s) of group (A) and the compound(s) of group (B) is between 1:100 and 1:1.

12. The method of claim 7, wherein the composition contains between 0.0001 and 0.05 weight percent of the compound(s) of group (A).

* * * * *